United States Patent
Bendek et al.

(10) Patent No.: US 10,434,262 B2
(45) Date of Patent: Oct. 8, 2019

(54) DEVICE AND METHOD FOR DELIVERING A MEDICAMENT

(71) Applicant: CAREBAY EUROPE LTD., Sliema (MT)

(72) Inventors: Antonio Bendek, Wellington, FL (US); Lucio Giambattista, Lighthouse Point, FL (US)

(73) Assignee: SHL MEDICAL AG, Zug (CH)

( * ) Notice: Subject to any disclaimer, the term of this patent is extended or adjusted under 35 U.S.C. 154(b) by 405 days.

(21) Appl. No.: 15/371,469

(22) Filed: Dec. 7, 2016

(65) Prior Publication Data

US 2017/0080163 A1 Mar. 23, 2017

Related U.S. Application Data

(63) Continuation of application No. 15/116,418, filed as application No. PCT/EP2015/054365 on Mar. 3, 2015, now abandoned.

(Continued)

(30) Foreign Application Priority Data

Mar. 25, 2014 (SE) ..................................... 1450345

(51) Int. Cl.
*A61M 5/32* (2006.01)
*A61M 5/20* (2006.01)
(Continued)

(52) U.S. Cl.
CPC ............ *A61M 5/3245* (2013.01); *A61M 5/20* (2013.01); *A61M 5/2033* (2013.01); *A61M 5/24* (2013.01);
(Continued)

(58) Field of Classification Search
CPC .... A61M 5/2033; A61M 5/20; A61M 5/3204; A61M 5/3287; A61M 5/31551;
(Continued)

(56) References Cited

U.S. PATENT DOCUMENTS 5,478,316 A 12/1995 Bitdinger et al.
7,112,187 B2 9/2006 Karlsson
(Continued)

FOREIGN PATENT DOCUMENTS

| WO | 2006/057604 | 6/2006 |
|----|-------------|--------|
| WO | 2010/066592 | 6/2010 |
| WO | 2011/139212 | 11/2011 |

OTHER PUBLICATIONS

International Search Report and Written Opinion for Int. App. No. PCT/EP2015/054365, dated Jun. 3, 2015.

*Primary Examiner* — Manuel A Mendez
(74) *Attorney, Agent, or Firm* — McDonnell Boehnen Hulbert & Berghoff LLP

(57) ABSTRACT

A device for delivery of medicament is presented that has an elongated housing, a container mounted within the housing and adapted to contain liquid medicament, a stopper slidably arranged within said container, and a delivery mechanism comprising a resilient member, a plunger assembly having one end connected to the stopper and a second end being operably connected to the resilient member, a rotatable latch for releasably retaining the plunger assembly in a first position where the resilient member has an accumulated energy, where rotation of the latch releases the plunger assembly such that the accumulated energy is transferred to the plunger assembly for driving the stopper within the container whereby the medicament within said container is delivered to an injection site. After delivery of the medicament a rotator having a hard stop feature aligns with a rib on (Continued)

the protective shield to prevent retraction of the protective shield.

20 Claims, 7 Drawing Sheets

Related U.S. Application Data

(60) Provisional application No. 61/948,716, filed on Mar. 6, 2014.

(51) Int. Cl.
*A61M 5/46* (2006.01)
*A61M 5/24* (2006.01)
*A61M 5/315* (2006.01)
*A61M 5/31* (2006.01)

(52) U.S. Cl.
CPC .... *A61M 5/31501* (2013.01); *A61M 5/31578* (2013.01); *A61M 5/3202* (2013.01); *A61M 5/326* (2013.01); *A61M 5/46* (2013.01); *A61M 5/31591* (2013.01); *A61M 2005/202* (2013.01); *A61M 2005/2013* (2013.01); *A61M 2005/3125* (2013.01); *A61M 2005/3126* (2013.01); *A61M 2005/3247* (2013.01); *A61M 2005/3267* (2013.01); *A61M 2205/581* (2013.01); *A61M 2205/582* (2013.01); *A61M 2205/583* (2013.01)

(58) Field of Classification Search
CPC ............ A61M 5/3202; A61M 5/31501; A61M 5/3157; A61M 5/31585; A61M 5/31571; A61M 5/3158; A61M 5/3245; A61M 5/326; A61M 5/2066; A61M 5/31535; A61M 5/31515; A61M 5/31541; A61M 5/14546; A61M 5/31578; A61M 5/46; A61M 5/31591; A61M 2005/2013; A61M 2005/3247; A61M 2005/202; A61M 2005/31501; A61M 5/3125; A61M 2005/3126; A61M 2205/581; A61M 2205/582; A61M 2205/583; A61M 2005/3267
See application file for complete search history.

(56) References Cited

U.S. PATENT DOCUMENTS

| | | |
|---|---|---|
| 7,125,395 B2 | 10/2006 | Hommann et al. |
| 8,460,245 B2 | 6/2013 | Guillermo et al. |
| 2007/0021720 A1 | 1/2007 | Guillermo |
| 2009/0112163 A1 | 4/2009 | Bivin et al. |
| 2010/0249721 A1 | 9/2010 | Guillermo et al. |

DEVICE AND METHOD FOR DELIVERING A MEDICAMENT

CROSS REFERENCE TO RELATED APPLICATIONS

The present application is a continuation of U.S. patent application Ser. No. 15/116,418, filed Aug. 3, 2016, which is a U.S. National Phase Application pursuant to 35 U.S.C. § 371 of International Application No. PCT/EP2015/054365 filed Mar. 3, 2015, which claims priority to U.S. Provisional Patent Application No. 61/948,716, filed Mar. 6, 2014 and Swedish Patent Application No. 1450345-2 filed Mar. 24, 2014. The entire disclosure contents of these applications are herewith incorporated by reference into the present application.

TECHNICAL FIELD

The present invention relates to a device and method for delivering medicament to a patient from a container mounted within the device. The device is adapted to automatically perform the delivery by requiring only that the user push the device against an injection site. The driving force needed for delivery is supplied by a coiled tension spring that is triggered by a rotating latch. A lockout mechanism is provided to prevent retraction of a protective shield after delivery.

BACKGROUND

Devices for the delivery of medicament in an automatic way e.g. auto-injectors, are known as convenient and safe devices for patients to self-administer various drugs themselves. For safety reasons, primarily to guard against needle sticks, many devices for the delivery of a medicament include covers and other components that protect users before and after use of the injector. Although different devices for the delivery of medicament vary in their total feature sets, they all have a mechanism that delivers the contents of a preloaded, prefilled container automatically, i.e., without requiring a person to manually force the contents within a container through a delivery member, e.g., a needle or a nozzle, into the patient.

Auto-injectors are described in U.S. Pat. No. 5,478,316 to Bitdinger et al.; U.S. Pat. No. 7,112,187 to Karlsson; and U.S. Pat. No. 7,125,395 to Hommann et al.; U.S. Patent Application Publication No. 2007/0021720 to Guillermo; and International Publication No. WO 2006/057604 by Olson, for example. The automatic delivery mechanism in a device for the delivery of medicament usually includes a compressed helical compression spring that drives a plunger rod forward as the spring decompresses upon activation of the device. In some designs, such springs work well. A fully compressed helical spring provides a force that is large enough to overcome the static friction between the plunger and the inner wall of a container, so called break loose force, and the spring at its full extension, which is often not at its full decompression, provides a force that is large enough to complete the injection stroke but causing the probability of the container breakage.

A challenge in the design of such springs is balancing the need for sufficient force at the end of stroke against the need for a not-too-large force during storage (when the spring is fully compressed) that may overload the other components in the device. Such other components may be made of plastics, glass or similar materials that have limited strengths.

Thus, the drive mechanism in such a device for the delivery of medicament should meet the following simultaneous goals: 1) exert enough force to overcome the "break loose" force of the container stopper and initiate delivery of the medication, 2) exert enough force to complete—the injection stroke, 3) meet goals 1) and 2) in an acceptable time frame (usually a few seconds), and 4) exert a low force during storage.

Rather than use typical helical compression springs, some delivery devices use constant force springs or even variable force springs in an attempt to meet the goals mentioned above. For example, in our earlier issued U.S. Pat. No. 8,460,245, such variable force tension springs are discussed.

Although constant-force or variable springs are better able than compression helical springs to meet the design goals of injector devices, there is also a need to provide a smooth and reliable way to trigger the device to initiate the injection process. Visually indicating the start of the injection process and showing the progress of the injection are also important in the design of a medicament delivery device, such as an auto-injector. Likewise, after the injection is complete it is important for safety reasons to protect the user and others by preventing accidental needle sticks. Preferably, the covering of the used needle should be automatic and nonreversible. In other words, the design should not require the user to perform any manual manipulation of any component of the device, especially components located at the distal or needle end of the device. Our invention addresses these concerns while employing a variable force spring as the driving force to perform the injection.

SUMMARY

One object of the present invention is to provide an automatic medicament or drug delivery device, which during delivery applies a predetermined sequence of at least two different force profiles to a container stopper, which ensures an optimal functionality of the device. This design lowers the risk of damaging the container and/or the device during medicament delivery and reduces the problems with plastic deformation of the plastic materials of the delivery device in comparison with prior art automatic medicament delivery devices.

Another object is to allow the user to control the manual insertion of the needle into the patient's skin while simultaneously pushing a needle shield into the device housing. The retraction of the needle shield occurs as the syringe needle penetrates the skin. When a predetermined depth of needle penetration is achieved, the needle shield retraction is complete and the injector is automatically triggered. This is referred to as the "triggering point." Triggering or firing of the injector is achieved when one or more proximal extending beams on the needle shield engage cam surfaces on a rotatable latch. The camming action insures a smooth rotation of the latch and avoids the abrupt triggering exhibited by prior injector designs. The rotation of the latch caused by the engagement of the beams disengages a locking protrusion from an indent on the plunger. As the protrusion moves from the indent into a longitudinal groove on the plunger, the plunger is released to move distally through the latch without obstruction. An uncoiled tensed plunger spring rewinds forcing a plunger rod to press against the syringe stopper, which begins the medicament delivery.

The plunger spring is part of the variable force drive mechanism of the injector and is preferably a variable force spring that can generate a predetermined sequence having at least two different force profiles only during a medicament delivery. Varying the wind, cradling, width or thickness of the band material of the spring or varying the Modulus of Elasticity of the material used to fabricate the spring can impact the force profiles of the sequence. Selecting the working material in different portions or laminating other materials onto a base material in different portions, etc. can also achieve this. The predetermined sequence of the variable force spring comprises a last force profile, which is a profile where the force increases; therefore, the medicament delivery device will have an advantage of completely emptying all of the medicament a container or syringe.

The auto-injector of the present invention also contains a visual indication mechanism that reliably and positively provides visible information and feedback to the user that the injection process is progressing and when it is completed. This visual indication mechanism comprises a flexible band arranged with different indications, wherein the band is rolled on a scroll and connected to the plunger on the opposite side of the scroll. When the plunger rod is released from its non-delivery state, the flexible band is pulled distally by the moving plunger assembly and indicates the status information to the user by the related printing on the flexible band.

Yet another object of the invention is the prevention of accidental needle sticks, which is achieved through a combination of a retractable needle shield and a rotator. Longitudinal ribs arranged on an outside surface of the needle shield cooperate with grooves arranged on the inner sidewall of the rotator. When the needle shield is pushed into the device housing during needle penetration, i.e., retracted, the rotator will be twisted or slightly rotated due to the interaction between the rib and the groove. After injection, the user removes the device from the injection site and the needle shield will fully extend to cover the syringe needle under the force of a needle shield spring. As the needle shield reaches the fully extended position the rotator again slightly rotates in the same direction to cause alignment of one or more hard stops located at the distal end of the channels with one or more bearing surfaces located at the proximal end of the ribs. This alignment prevents the rib (and the needle shield) from moving axially, thus preventing retraction of the needle shield and exposure to the used needle. The combination of the hard stop and bearing surface of the rib form an irreversible lock of the needle shield.

The above-mentioned objects, along with other objects described below, are accomplished with a delivery device comprising an elongated housing, a container of medicament mounted within the housing having a slidable stopper, and a non-rotating plunger assembly in contact with the stopper. The plunger rod has an indent and a longitudinal groove and is configured to move axially relative to the housing from a ready position and to an end-of-injection position. There is a non-rotating needle shield axially slidable with respect to the housing that has an outer surface comprising a longitudinal rib terminating in a bearing surface, where the needle shield has a proximally extending beam and is configured to move from a partially extended position, to a retracted position and to a fully extended position.

The device also includes a rotator configured as a cylindrical tube having an open distal end and a proximal end wall, where the rotator is axially fixed inside the housing and is rotated through engagement with the rib to form an irreversible lock to prevent the needle shield from moving when in the fully extended position. The rotator can also have a longitudinal channel on an inside surface configured to accept axial movement of the rib. A through hole is provided in the proximal end wall to allow the needle shield beam to pass through to engage the latch. The rotator channel preferably has straight and angled side walls configured to engage the rib when the rib moves in the proximal direction such that engagement of the bearing surface of the rib with the angled sidewall imparts a first biasing force that causes the rotator to rotate relative to the housing to a first position where the flexible tooth partially indexes from one ratchet tooth to an adjacent ratchet tooth. The proximal end wall of the rotator preferably has a set of circumferentially arranged ratchet teeth configured to engage a flexible tooth on the latch carrier such that the engagement of the ratchet teeth with the flexible tooth creates a second biasing force urging the rotator to rotate from a first to a second position. The partial indexing creates a rotational biasing force that ultimately causes the rotator to complete a second slight rotation that aligns the hard stop with the rib to lock out the needle shield.

The drive mechanism is powered by a coiled spring having a proximal distal end fixed axially relative to the outer housing and a proximal end attached to the plunger assembly such that the coiled spring is in an extended partially uncoiled tensed configuration having accumulated energy when the plunger assembly is in a cocked position. To release the drive mechanism, i.e., firing the device, a rotatable latch is used having a first position where the latch prevents the plunger assembly from moving axially and a second position where the latch is disengaged from the plunger assembly to allow the plunger to axially move distally relative to the latch, the rotator and the outer housing such that the accumulated energy is transferred to the plunger rod for driving the plunger rod and the stopper a predetermined axial distance within the container whereby the medicament within said container is delivered. The latch has a cam configured to engage a bearing surface on a proximal end of the needle shield beam. The cam can be configured with a cam angle such that proximal axial movement of the beam when engaged with the cam causes a smooth and non-abrupt rotation of the latch to rotate from the first position to the second position. The latch preferably has through hole to accept axial movement of the plunger rod and has an inwardly projecting protrusion configured to engage an indent on the plunger rod when the latch is in the first position to prevent axial movement of plunger relative to the housing. The plunger rod can also have a longitudinal groove configured to accept the protrusion when the latch is in the second position, thus allowing unimpeded axial movement of the plunger rod relative to and through the latch.

To allow the user to see the progress of the delivery the proximal end of the housing comprises a window that allows a user to visually observe a scrolling tape that moves during the delivery of the medicament. The device also can contain a latch carrier axially fixed to the housing, where the latch is rotatably positioned in the latch carrier and the latch carrier has a through hole to allow passage of the proximally extending beam on the needle shield as the needle shield moves in a proximal direction. The needle shield is preferably connected to a biasing element that urges the needle shield to move distally such that a portion of the shield protrudes from the distal end of the housing when the plunger assembly is in the ready position. A clicker mechanism generates an audible sound during the delivery of the medicament and preferably comprises a clicker arm on the plunger assembly that engages teeth on a clicker track that is axially fixed relative the outer housing.

Using the medicament delivery device described herein, the present invention includes a method of performing an injection comprising, in combination, the following steps,
a) placing a needle shield at an injection site, where the needle shield is partially extended from a distal end of a housing of an auto-injector;
b) pushing the housing in a distal direction to retract the needle guard into the housing to a fully retracted position, where the needle guard has a beam projecting proximally and a longitudinal rib on an outside surface that engages a channel on a rotator that is axially fixed to the housing;
c) engaging the beam with a rotatable latch when the needle guard is in the fully retracted position causing the latch to rotate and unlock a plunger rod;
d) coiling a variable force spring attached to the plunger rod to axially move the plunger rod distally where it engages a slidable stopper in a container of medicament to deliver the medicament by injection into the injection site;
e) extending the needle shield to a fully extended locked position when moving the housing proximally from the injection site and; and
f) rotating the rotator to align the rib with a hard stop on the rotator when the needle shield is in the extended locked position to prevent retraction of the needle shield into the housing.

The method can also include the engagement of the rib with the channel to rotate the rotator relative to the housing partially indexing a ratchet engagement between the rotator and a rotatably fixed latch carrier creating a biasing force that results in a second and final rotation of the rotator when the needle guard is in the fully extended position.

According to another aspect of the present invention, the last force profile in the sequence is a profile where the force increases. The variable force spring is a coil spring of band material and wherein the different force profiles are obtained by suitably adjusting the material and/or the geometry and/or the natural radius and/or the elastic modulus of the spring. The variable force spring has one end attached to a latch carrier which is fixedly arranged to the housing and a second end, which is variably wound, cradled on the proximal end of the plunger.

These and other aspects of the invention and advantages with the present invention will become apparent from the following detailed description and from the accompanying drawings.

BRIEF DESCRIPTION OF THE FIGURES

The invention will now be described in more detail and with reference to the appended drawings in which.

DETAILED DESCRIPTION

In the present application, when the term "distal part/end" is used, this refers to the part/end of the delivery device, or the parts/ends of the members thereof, which under use of the delivery device, are located the closest to the medicament delivery site of the patient. Correspondingly, when the term "proximal part/end" is used, this refers to the part/end of the delivery device, or the parts/ends of the members thereof, which under use of the delivery device, are located the farthest from the medicament delivery site of the patient. So, for example, the cap of the reusable auto-injection training device described herein is located at the distal end of the training injector and the ribbon window is located at the proximal end. As used herein, the term "container" encompasses all types of medicament containers that are commercially available that are suitable for injectable liquid compositions, including prefilled syringes, cartridges and ampoules.

Figure 1:
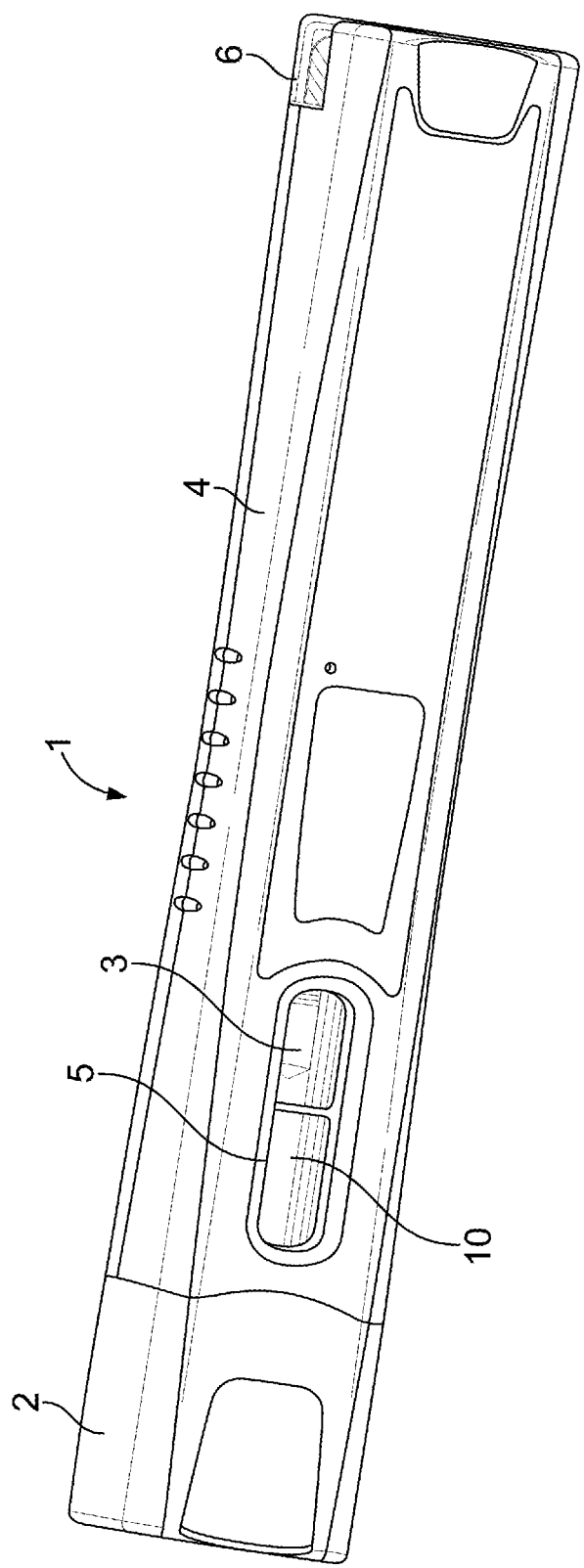
FIG. 1 is a perspective view of an embodiment of the medicament delivery device according to the invention shown as an auto-injector in the fully assembled state.
Figure 3:
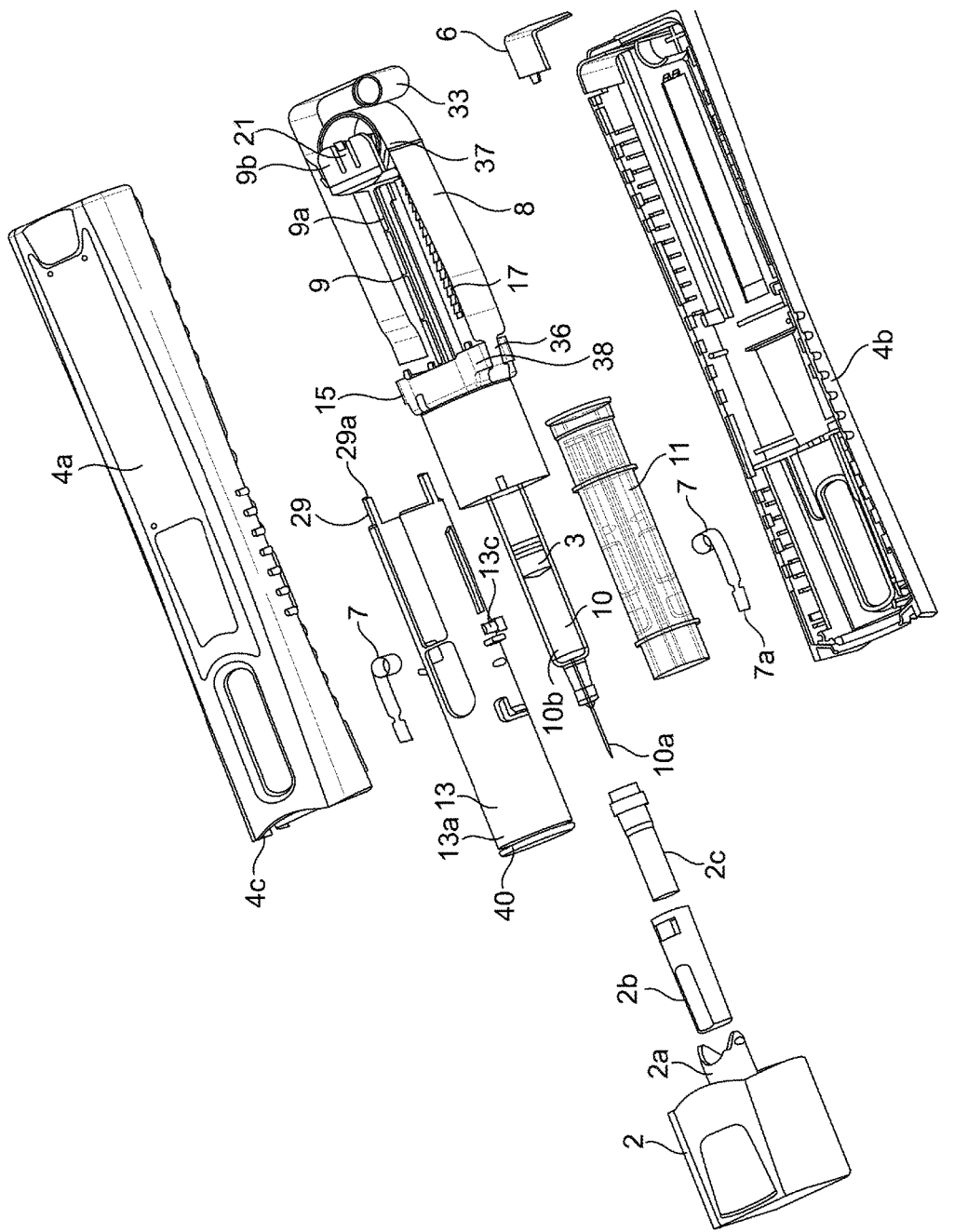
FIG. 3 is a perspective exploded view of the embodiment of FIG. 1 in a disassembled state.

In one embodiment the invention relates to an auto-injection device 1 as best shown in in FIGS. 1 & 3 comprising a housing or outer body 4 and a removable cap 2. Cap 2 includes a needle cover remover 2a that is configured to grab and remove rigid cover 2b and associated flexible needle cover 2c from attachment to the distal end of syringe barrel 10 having fixed thereto needle 10a when the cap 2 is pulled off housing 4. Housing 4 has window or cut-out 5 that allows visual observation of the syringe barrel 10 and slidable stopper 3 contained within the syringe barrel. As the medicament delivery process progresses a user can watch the stopper slide axially in the distal direction.

The outer body or housing 4 has a scroll window 6 located at the proximal end where the housing 4 is preferably comprised of an upper body housing 4a and a lower housing body 4b, each preferably comprising a thermoplastic material. These two body housings can be attached during manufacturing by pins, tongue & groove, snap fit, glue, fasteners, welding or any other known process to provide a secure connection.

A coiled spring 8 provides the driving force that moves plunger assembly 9 distally to move slidable stopper 3 within syringe barrel 10 to dispense medicament 10b from needle 10a. One end of spring 8, i.e., the distal end 36, is attached to latch carrier 15 through connectors 38. Latch carrier 15 is axially fixed to the lower housing 4b such that there is no relative movement between the latch carrier 15 and the housing 4. This provides a fixed or anchor position for the distal end 36 of plunger spring 8. Because spool 37 that is attached to the proximal end of spring 8 is fixed to the proximal end 9b of the plunger assembly 9, the spool 37 and attached spring 8 will move relative to the distal end 36 of the spring and the latch carrier 15 as it rewinds or coils to a relaxed state. As the plunger assembly 9 is moved proximally to cock the device during manufacturing, spring 8 is unwound from spool 37 and is in an extended state having accumulated energy stored therein. This unspooling or unwinding of the band material used to form spring 8 creates a tension or winding force in the plunger spring 8 tending to oppose the proximal setting movement of the plunger assembly during manufacturing and assembly of the device. This winding force tends to pull the plunger assembly back in the opposite or distal direction in order to rewind, i.e., coiling, the spring around spool 37. This winding force is the driving force that allows the plunger rod 9a to move distally during medicament delivery or in the case of the auto-injector embodiment illustrated, perform an injection.

Spring 8 is preferably a variable force spring and is not a traditional helical compression spring made from a helix of wire. Spring 8 is preferably a flat or band spring formed in coil. More preferably spring 8 is not a constant-force spring (CFS). With CFSs, force, or load, is a function of material width, thickness, and coil diameter. The load, which is directly proportional to the material width in a CFS and not directly proportional to material thickness, is given by the following expression:

$$P = Ebt3 \ 126,4R2 \quad \text{Eq. 1}$$

in which P is the load, E is the material's Modulus of Elasticity, b is the width of the material, t is the thickness of the material, and R, is the natural radius. If the elastic modulus is given in units of pounds per square inch (psi) and the material width, thickness, and natural radius are given in inches, then the load is given in pounds (lb). Of course, other systems of units can be used.

As mentioned spring 8 is preferably a variable-force spring (VFS) configured as a coil of band material that exerts a predetermined sequence of at least two different force profiles. There are three types of force profiles. A first force profile is a profile where the force decreases as the spring relaxes. A second force profile is a profile where the force increases as the spring relaxes. A third force profile is a profile where the force is constant as the spring relaxes. As just one of many possible examples, changing the radius of the coil, yielding a spring that exerts either increasing or decreasing force, is advantageous in a wide range of products, including devices for delivery of medicament. Instead of varying the natural radius, i.e., the radius of the coil, it is possible to make VFSs that exert a predetermined sequence of at least two different force profiles by modifying the other parameters in Eq. 1, e.g., the physical shape of the spring. Increasing, either the material's thickness or the width or both. Preferably, the VFS is configured to yield a spring that generates an increasing force as the spring relaxed, i.e. coils. Varying the width of the material used to fabricate the VFS produces the desired load profile.

The parameters in Eq. 1 can be manipulated in various ways as necessary for the application of the VFS. For example, besides or instead of varying the width of the band material, it is possible to vary the material's thickness and/or the elastic modulus. The load exerted by a VFS increases more by doubling the thickness than by doubling the width. The elastic modulus in different portions of the material can be varied in many ways, for example by selectively working the material in such portions, laminating other materials onto a base material in such portions, etc. A preferred approach is to vary the radius of the coil of the spring material. The VFSs used in the present invention are advantageous to overcome problems due to siliconization profiles of the stopper syringe wall interface, especially at the end of the delivery stroke. The VFSs described here enable the spring forces generated to match or compensate the break-loose and glide force profiles within the container generated by different manufacturers and processes better than conventional compression springs.

Preferably, the plunger spring 8 is composed of spring steel, plastic with memory, or other material that can be unwound with an applied force during manufacturing and assembly of the auto-injector and has self-rewinding property that uses the stored applied force generated when the device is set to the ready to inject state. As mentioned, preferably the spring has a constant or variable force profile. Preferably, the spring of the present invention has a variable force profile comprising a constant force section of about 13N±10% and variable force section that provides approximately 17.4N±10% of force. The springs used in present invention are also known as torsion flat springs that are typically made of metal because of the minimum amount of deformity and characteristic changes that occur using metal. The common metal used is stainless steal or equivalent metal, which will have the precise repeatability of the desired force in a very short distance uncoiling motion while maintaining its full integrity and characteristic as it is repeatedly uncoiled and coiled with a specific constant torsion force. These types of springs require less space than a compression spring made form a helix of wire and thus can be designed for placement in the device in very short and tight areas where a compression spring would not fit.

Figure 2:
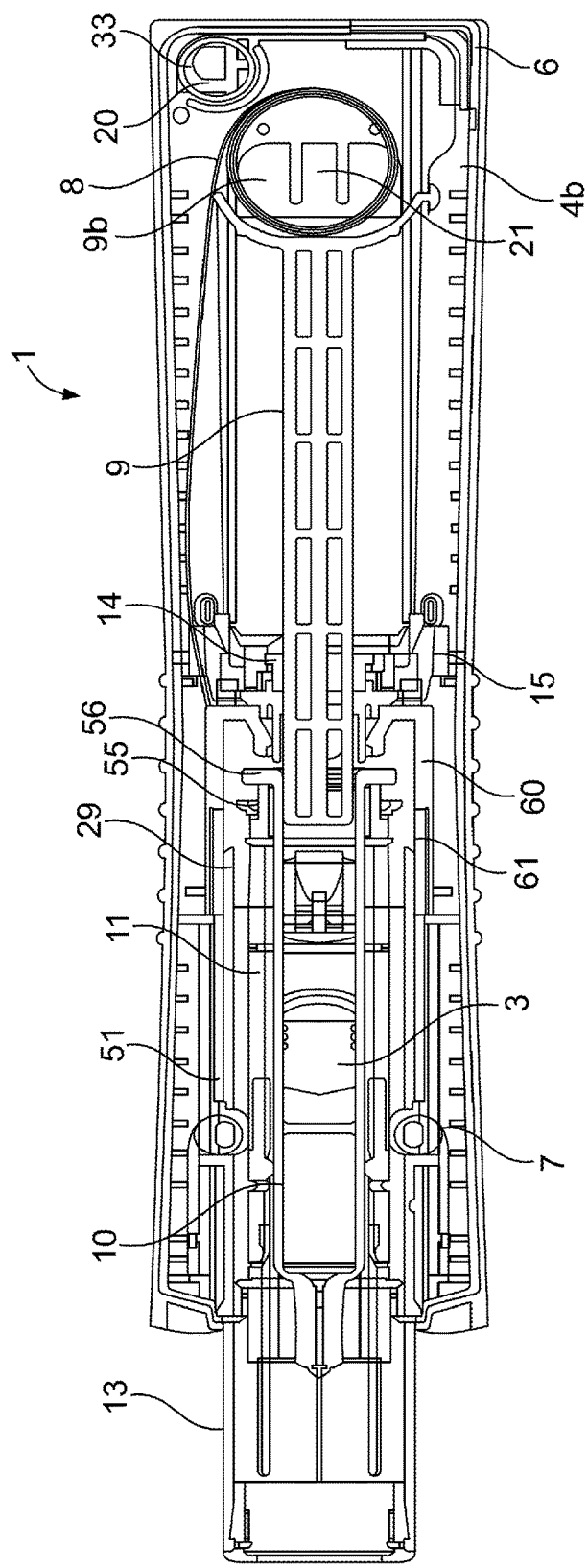
FIG. 2 is a cross-sectional view of the embodiment of FIG. 1 in a partially disassembled state.

Similar in design to the plunger spring 8 is shield spring 7 as shown in FIGS. 2-3. This spring 7 is used to bias the protective or needle shield 13 in a first stand-by position where the distal end 13a, with attached shield ring 40, protrudes out of the distal end 4c of housing 4. The distal end 7a of spring 7 is fixed to housing 4b and the proximal end or the coil of spring 7 is fixed to a post or protrusion 13c on the outer surface of shield 13. In a preferred embodiment the shield springs 7 comprise two constant force springs. These springs can also be replaced by another kind of resilient means, e.g., a coil spring, a spiral spring. The wound or coiled ends of the springs are cradled within the outwardly annular ledge 13c and the other end of the spring is secured to housing 4.

Protective or needle shield 13 covers or shields the needle from the user's view and provides user protection from accidental needle sticks, both before and after the injection is completed. Shield 13 is configured to slide axially relative to housing 4, but is rotationally fixed relative the housing. To move the shield 13 from the stand-by or ready position to an activate or injection position, the user places the shield ring 40 against an injection site and pushes or moves the housing distally towards the injection site. This causes the needle shield 13 to slide or retract proximally relative and into the housing 4 until fingers or beams 29 engage latch 14 (see FIGS. 4 & 7). This engagement of beams 29 with latch 14 occurs through finger through holes 65 and 30 located on rotator 60 and on latch carrier 15, respectively. As the shield 13 slides proximally, springs 7 are unwound from the proximal coil end attached to the shield 13 thus creating a tensioning force similar in nature to the spring force described above in relation to the unwinding of plunger spring 8 when the plunger assembly 9 is set during the assembly of the device 1. This tensioning or winding force urges spring 7 to rewind itself pulling or urging shield 13 in the distal direction. Once the shield 13 has reached the activate position the distal end of shield ring 40 becomes approximately flush with the distal end 4c of housing 4.

Figure 6:
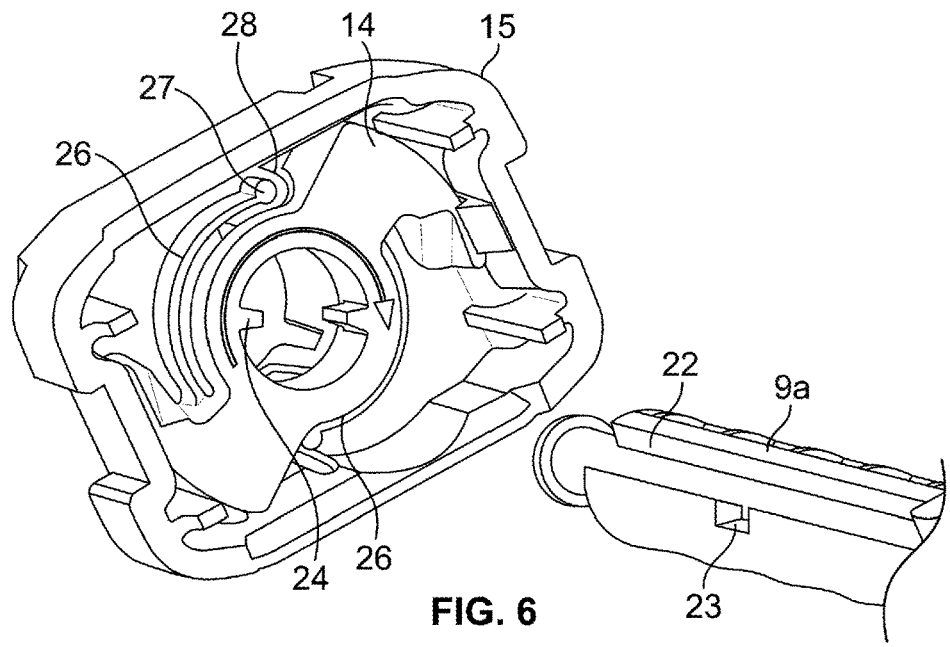
FIG. 6 is a close-up perspective view looking distally of the plunger rod, latching carrier and latch.
Figure 7:
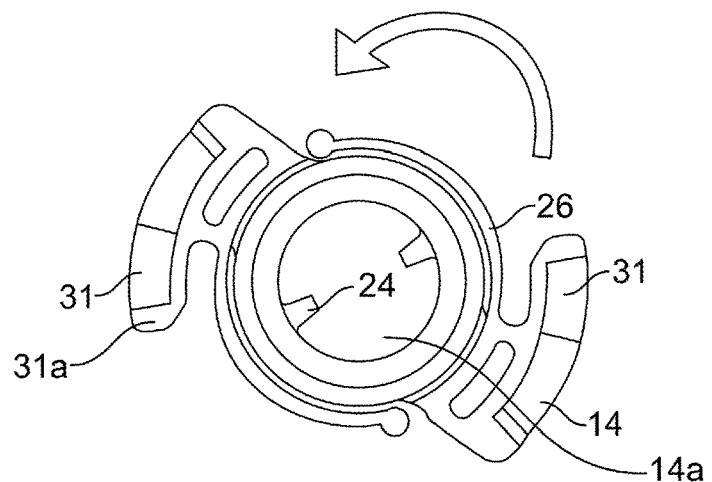
FIG. 7 is a close-up perspective view looking proximally of the latch disassembled from the latch carrier.
Figure 7:
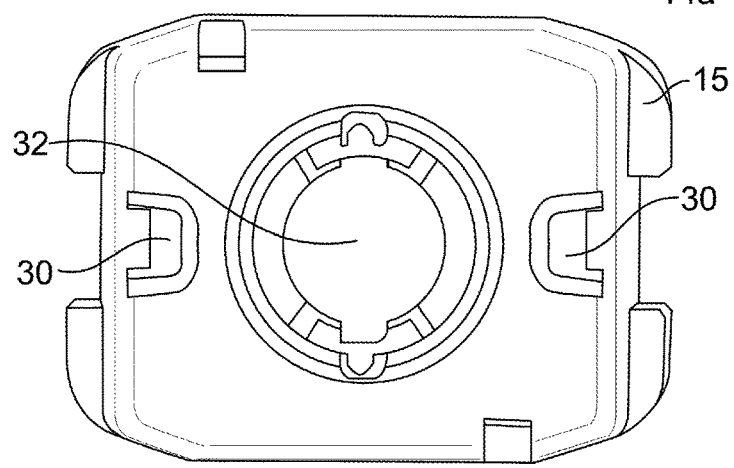

In arriving at the activate or triggering position, the needle shield beams 29 have a bearing surface 29a that contacts latch cam 31 on the angled cam surface 31a in a bearing surface relationship where the angled cam surface slides and rotates relative to the bearing surface 29a at the proximal end of the beam 29. (see FIGS. 4 & 7). Since the needle shield 13 is rotationally fixed relative to the housing 4, this bearing contact causes latch 14 to rotate counterclockwise when viewed in the proximal direction as shown in FIG. 7. As shield 13 cannot rotate the fingers impart a rotating motion of latch 14 relative to latch carrier 15, which is also rotationally and axially fixed to the housing 4. Spring arms 26 on latch 14 engage catches 28 of the proximal inside surface of latch carrier 15 through spring stops 27 as shown in FIG. 6, as the latch 14 is rotated in the direction shown by the arrow in FIG. 6, the spring arms 26 provide a counter biasing or return force that urges the latch 14 to counter-rotate in the opposite direction. Latch 14 has a plunger through hole 14a that has an inner surface generally matching the external diameter or shape of plunger rod 9a. This inner surface has one or more radial extending protrusions or keys 24 extending inward and configured to engage plunger rod 9a in either a key notch or indent 23 or a longitudinal slot or groove 22. When two keys 24 are used as illustrated in FIG. 7, there will be two notches 23 and two slots 22, each preferably diametrically opposed from each other.

When the plunger assembly 9 is pushed back and set to the ready position during manufacturing and assembly of the device, notch or indent 23 on plunger rod 9a slides relative to protrusion 24. Initially the protrusion 24 is positioned in longitudinal slot or groove 22 on plunger rod 9a, which allows the plunger rod to move axially relative to the latch 14 positioned in latch carrier 15. As plunger assembly 9 and notch 23 moves proximally during the initial setting of the device, the notch 23 will eventually become adjacent to protrusion 24. At that moment, because of the counter rotation force imparted by spring arms 26 this will cause the latch protrusion 24 to rotate into notch 23. This notch or indent is positioned longitudinally along the plunger rod 9a such that the latching of the protrusion and the notch 23 occurs when the plunger assembly 9 has reached the fully cocked position. Although in this cocked position the plunger spring 8 is fully tensioned and urging the plunger assembly to move axially in the distal direction, the engagement of protrusion 24 with notch 23 prevents or prohibits axial movement in either direction. As shown by the direction arrow in FIG. 6, the latch must rotate clockwise (when viewed distally) in order to disengage the protrusions 24 from the notches 23 to drop into and engage grooves 22. This occurs, as previously described, when fingers 29 contact cams 31 and rotate latch 14 in the direction illustrated by the arrow. Rotation of latch 14 is caused because cam 31 has an angled surface 31a. Once protrusions 24 rotate into grooves 22 there is no stop or other obstruction in the groove to prevent plunger rod 9a from moving distally relative to latch 14, protrusion 24, and latch carrier 15.

Figure 4:
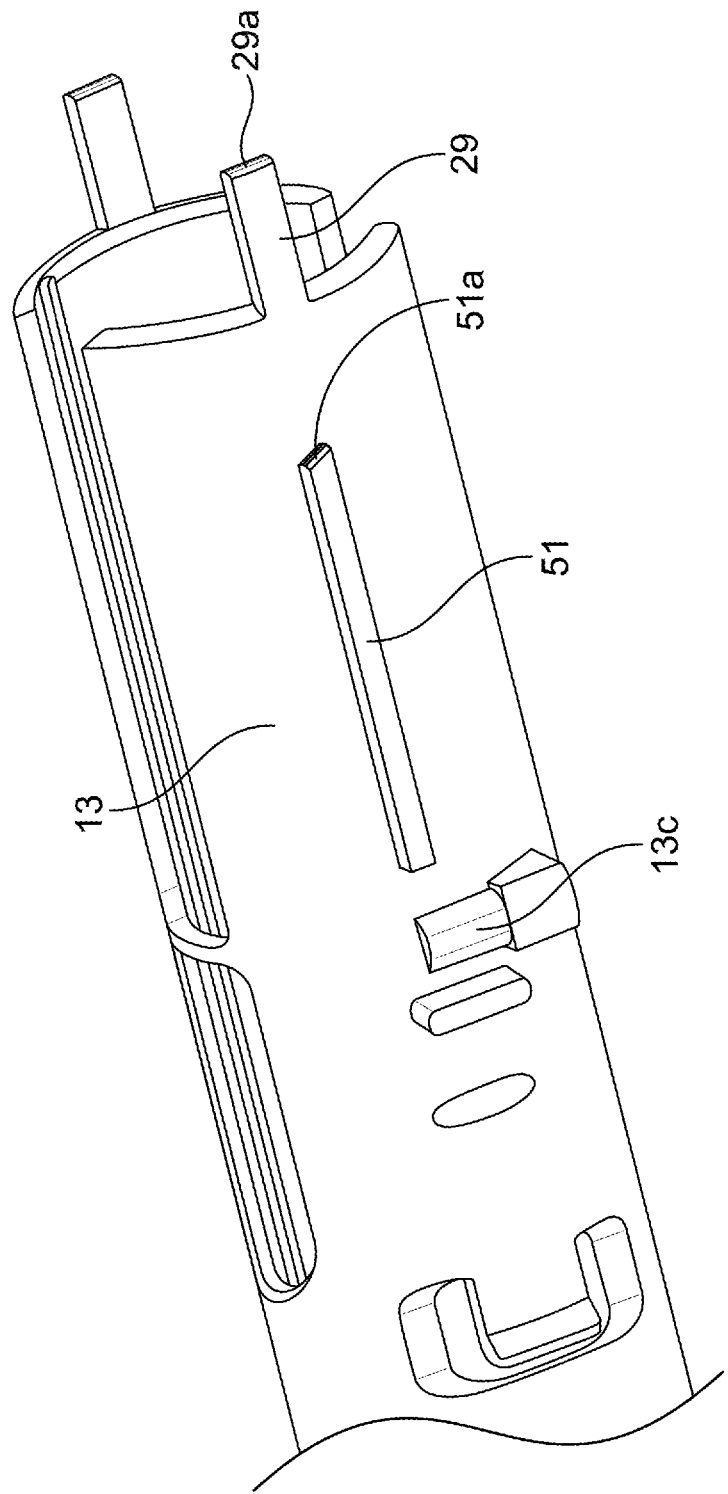
FIG. 4 is a perspective view of the needle shield of the embodiment of FIG. 1.
Figure 5:
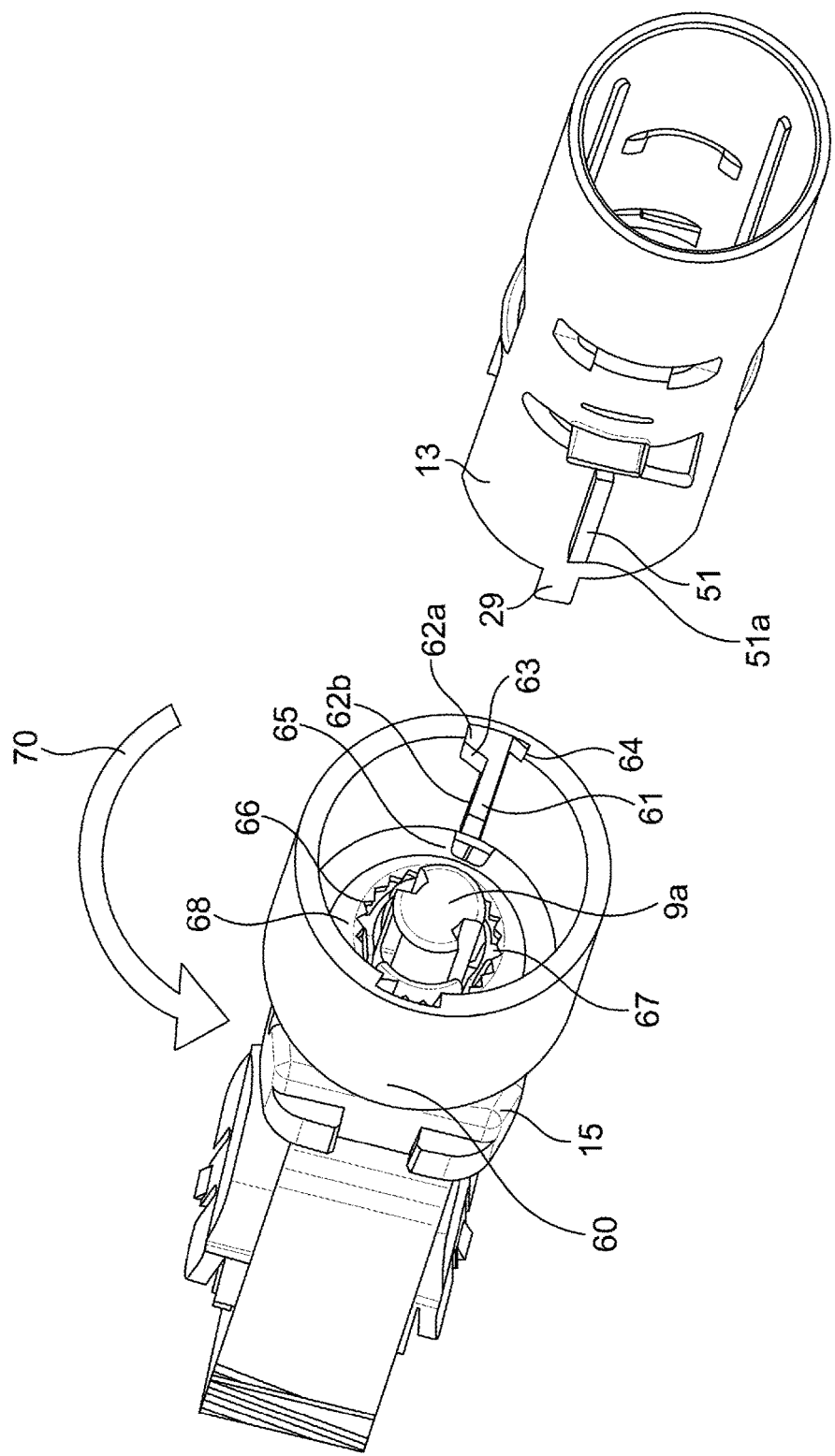
FIG. 5 is a perspective view of the needle shield, plunger assembly, latch carrier and rotator of the embodiment of FIG. 1

Another feature of the present invention is rotator 60 as best illustrated in FIGS. 2 and 5. The rotator 60 provides a safety feature to the device in that at the end of the delivery or injection sequence or process the rotator moves (rotates) relative to the housing 4 such that the needle shield 13 is irreversibly locked in a fully extended position covering the used needle. The rotator provides a hard stop 64 as explained below that prevents the needle shield from retracting proximally into the housing. As such, the user and others are protected against accidental needle sticks. Referring to FIG. 4, one or more ribs 51 are located on the outside surface of needle shield 13 that terminate in a bearing surface 51a. Preferably these ribs are integral to the shield and are formed during the molding process used to fabricate shield 13. As the needle shield is pushed into the housing during the injection process, the bearing surface 51a first engages sidewall 62a and then engages angle sidewall or ramp 63. (see FIG. 5). Because the needle shield is rotatably fixed with respect to the housing it cannot turn so therefore the interaction of bearing surface 51a with ramp 63 causes the rotator 60 to rotate slightly in the direction shown by the arrow 70. With the bearing surface 51a in channel 61 and the rotator now stationary, the needle shield rib 51 continues to travel along sidewall 62b as shield 13 is further pushed or retracted into housing 4 moving proximally. Eventually, fingers or beams 29 will pass through a through hole 65 in the proximal end wall 68 of rotator 60. Preferably there are two through holes 65 that align with two fingers 29. When fingers 29 contact latch 14 causing it to rotate, the piston rod 9a will move distally to complete the medicament delivery. When the user removes needle shield 13 from the injection site, the needle shield reverses direction and starts to extend from the housing moving distally carrying ribs 51 along channel 61 in the reverse direction. When the bearing surface 51a arrives at a point just outside of the distal end of channel 61 the needle shield is fully extended and covers the used needle. The bearing surface 51a is just outside of channel 61 allowing rotator 60 to further slightly rotate in the same direction as the first slight rotation such that the bearing surface 51a becomes aligned with hard stop 54 located at the terminal or distal end of channel 61. If the needle shield were to be pushed proximally in an attempt to retract the shield into the housing the bearing surface 51a would engage hard stop 64 and prevent any axial or retracting movement of the shield. In essence the combination of the bearing surface 51a and hard stop 64 forms an irreversibly lock against retraction.

The rotator essentially makes two small rotations during the medicament delivery process from start to end. Biasing forces are needed to cause both rotations. The first rotation results from the biasing force imparted by the bearing surface 51a contacting angled sidewall 63. As the rotator is forced to rotate, ratchet teeth 66 that are arranged circumferentially around a through hole that allows passage of plunger rod 9a, move out of engagement with one or more flexible teeth 67 located on a distally projecting extension of latch carrier 15. This first rotation of the rotator is not large enough to fully index the flexible tooth 67 into an adjacent ratchet tooth. This less than full indexing, i.e., partial indexing, imparts a second biasing force on the rotator as a result of the flexible tooth urging the rotator to continue in rotation in the direction of the first slight rotation caused by the first biasing force imparted by rib 51. This second biasing force remains as ribs 51 travels proximally and then distally in channel 61. When rib 51 disengages from channel 61 when the needle shield is allowed to fully extend out of the housing, the second biasing force causes the rotator to complete the second slight rotation such that the hard stop 64 becomes in axially alignment with bearing surface 51a. This second rotation of the rotator completes the formation of the irreversible lockout of the needle shield 13.

As stated, plunger spring 8 provides the driving force to move plunger assembly 9 axially in the distal direction when the medicament delivery device is fired or triggered by the user. No trigger button or switch is required to fire device 1 and, as such, there is no mechanism in the device that requires manipulation using the user's fingers to push, flip, de-latch, or otherwise activate in order to fire the device. All that is required to trigger the injection procedure is to press the shield 13 against an injection site.

The medicament container or pre-filled syringe 10 as illustrated in FIG. 3 is positioned in and held axially fixed by carrier 11. Carrier 11 is required because it provides an additional housing component for the syringe as well as an axial alignment feature for the syringe shield. The carrier also allows the medicament container to be held in a position where the container will have minimum rotation and or movement as a result of the activation or deactivation phases and repeated actions by a user. A syringe collar 55 is disposed between the syringe finger flanges 56 and carrier 11. (see FIG. 2). This collar provides a damping force or cushioning effect between the syringe and the carrier to avoid breakage of the syringe or the delivery device. The collar is preferably fabricated of a thermoplastic elastomer (TPE) or some other soft plastic that can absorb medicament delivery forces generated by spring 8.

Figure 8:
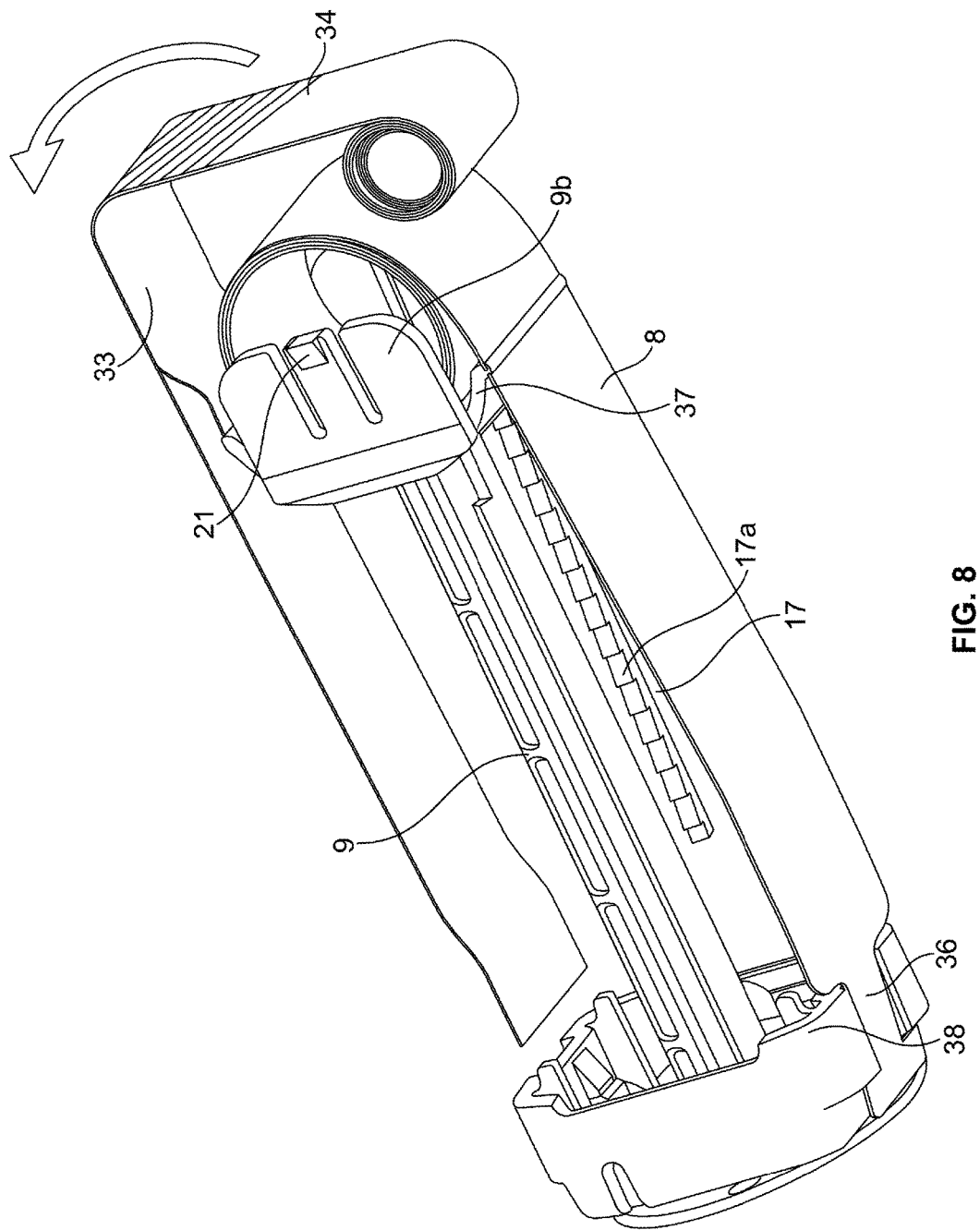
FIG. 8 is a perspective exploded view of the proximal portion of the plunger assembly with the attached tape and spring.

The medicament delivery device of our invention also generates an audible noise or signal to the user as the injection proceeds from the start to the end. This audible feature is achieved preferably by the use of a clicker track 17 fixed to the housing 4b and engaged by a flexible clicker arm 21 attached to plunger assembly 9. As illustrated in FIGS. 3 & 8, a preferred configuration uses two clicker arms 21 and two clicker tracks 17 diametrically opposed to each other. One clicker track is axially fixed and parallel to the longitudinal axis of the inside surface of housing 4b and the other clicker track is similarly axially fixed to the inside surface of housing 4a. One clicker arm 21 is located on the top portion of plunger assembly 9 as shown in FIG. 8 and the other clicker arm (not visible) is located on the underside or bottom of the proximal end 9b of plunger assembly 9 to engage the clicker track 17 shown in FIG. 8. As the plunger assembly moves distally during the injection process, the clicker arm engages the clicker track and rides up and over the teeth positioned longitudinally along the track 17 causing a "clicking" sound that is heard by the user. The teeth separation and configuration is selected such that each click preferably matches the delivery of a unit dose of the medicament from the pre-filled container. The design of the clicker arm 21 and clicker track 17 must take into account the setting of the device during assembly and, as such, must allow the plunger assembly to move in the opposite proximal direction during setting. In other words, the engagement of the clicker arm and clicker track must not be unidirectional, but instead must be bidirectional. Another feature of the clicker is that once the noise stops the user will know that the injection is complete or that the device has been fully set during assembly. Alternatively, the clicker track can have larger or different shaped teeth or a tooth at the distal end such that as the plunger assembly finishes moving distally the clicker arm will engage the larger/different tooth and make a louder or different noise signifying the end of the injection process.

The scroll window 6 located at the proximal end of housing 4 allows the user to watch a moving scroll of tape 33 unwind as the injection procedure is in progress. The window can be comprised of any clear, transparent or translucent material that will allow the user to see movement of tape 33. Preferably the window is constructed or formed as a lens to magnify the appearance of tape 33. The observation of the moving tape 33 provides a visual signal to the user of when injection begins, as it progresses, and when the injection ends. The progress scroll or tape 33 is mounted on scroll spindle 20 as illustrated in FIG. 2. Preferably, the tape 33 contains indicia 34 that provide the user with a visual signal through window 6 that the tape is moving in the direction of the arrow in FIG. 8 as the injection progresses.

Spindle 20 is fixed to lower housing 4b and is prevented from moving axially, but is allowed to rotate about the stationary fixed axial position. The end of the tape opposite spindle 20 is fixed or attached to plunger assembly 9 and moves axially in the distal direction as shown by the arrow in FIG. 8 during activation of the delivery or injection process. As the plunger assembly 9 moves distally it pulls tape 33 in the direction of the arrow thus unwinding the tape from spindle 20 and preferably revealing indicia 34, which in turn shows the user movement of the tape signaling that the injection process is progressing. At the completion of the injection sequence when the plunger assembly 9 has traveled to its terminal or final distal position, the tape 33 has been unwound from spindle 20 but remains connected to the spindle.

Preferably tape 33 is composed of a material that is resilient and has memory, like spring steel or a plastic composite with memory, such that as the plunger assembly 35 is set during manufacturing and assembly of the device, the tape will wind onto the spindle to the starting position. This winding process is analogous to that used in hand held tape measures that have automatic rewind features. Alternatively, the spindle may be connected to a biasing assembly or component, such as a spring, such that the biasing component is stressed or tensioned as the tape is unwound. During the initial setting of the plunger assembly such a biasing component causes the spindle to reverse rotation direction and winds the tape to the starting position.

It is to be understood that the embodiments described above and in the drawings are to be regarded only as non-limiting examples of the invention and that they may be modified in many ways within the scope of the claims. This application is therefore intended to cover any variations, uses or adaptations of the invention using its general principles. Further, this application is intended to cover such departures from the present disclosure as come within known or customary practice in the art to which this invention pertains.

The invention claimed is:

1. A device for the delivery of medicament, comprising:
   an elongated housing having a proximal end and a distal end;
   a container mounted within the elongated housing and having a slidable stopper contained within and configured to contain a liquid medicament;
   a plunger assembly comprising a proximal end and a distal end, the distal end configured to act on the stopper of the container,
   where the plunger assembly is configured to move axially;
   a needle shield axially slidable with respect to the housing, the needle shield being rotationally fixed relative to the housing and comprising at least one bearing surface,
   where the needle shield is configured to move from a first position to a second position;
   a rotator configured with an open distal end,
   where the rotator is fixed within the housing and is rotated through engagement with the bearing surface of the needle shield so as to form a lock that prevents the needle shield from moving when the needle shield is in the second position;
   a coiled spring having a one end fixed axially relative to the outer housing and a second end attached to the plunger assembly
   such that the coiled spring is in an extended partially uncoiled tensed configuration having an accumulated energy when the plunger assembly is in a cocked position;
   a latch having a first position where the latch prevents the plunger assembly from moving axially and a second position where the latch is disengaged from the plunger assembly to allow the plunger to move axially, such that the accumulated energy of the coiled spring is transferred to the plunger rod assembly for driving the plunger rod assembly and the stopper of the container.

2. The delivery device of claim 1 wherein the first position of the needle shield comprises a partially extended position and the second position of the needle shield comprises an extended position.

3. The delivery device of claim 2 wherein the needle shield is configured to move from a first position to an intermediate position.

4. The delivery device of claim 3 wherein the intermediate position of the needle shield comprises a retracted position.

5. The delivery device of claim 1 wherein the needle shield comprises an outer surface comprising a longitudinal rib terminating in the bearing surface.

6. The delivery device of claim 1 wherein the plunger assembly comprises a non-rotating plunger assembly.

7. The delivery device of claim 6 wherein the non-rotating plunger assembly comprises a plunger rod.

8. The delivery device of claim 7 wherein the plunger rod further comprises an indent.

9. The delivery device of claim 8 wherein the latch comprises an inwardly projecting protrusion configured to engage the indent of the plunger rod when the latch is in a first position so as to prevent axial movement of the plunger reassembly.

10. The delivery device of claim 9 wherein the plunger rod further comprises a longitudinal groove configured to accept the inwardly projecting protrusion when the latch is in the second position.

11. The delivery device of claim 1 wherein the plunger assembly is configured to move axially relative to the housing from the cocked position to an end-of-injection position.

12. The delivery device of claim 1 wherein the coiled spring comprises a distal end fixed axially relative to the outer housing and a proximal end attached to the plunger assembly.

13. The delivery device of claim 1 wherein the coiled spring comprises a variable force spring comprising a coiled band configured to move from an uncoiled tense state to a coiled relaxed state.

14. The delivery device of claim 1 wherein where disengagement of the latch from the plunger assembly allows the plunger to axially move distally relative to the latch, the rotator, and the outer housing.

15. The delivery device of claim 1 wherein the latch comprises a rotatable latch, rotatable from the first position to the second position.

16. The delivery device of claim 15 further comprising a latch carrier axially fixed to the housing,
where the latch is rotatably position in the latch carrier.

17. The delivery device of claim 16 wherein the latch carrier comprises a through hole that is configured to allow passage of a portion of the needle shield as the needle shield moves in a proximal direction.

18. The delivery device of claim 17 wherein the portion of the needle shield that passes through the through hole of the latch carrier comprises a proximally extending beam.

19. The delivery device of claim 1 wherein the plunger assembly is configured to move only axially in a distal direction.

20. The delivery device of claim 1 wherein the first position of the needle shield and the second position of the needle shield reside in a same extended position.

* * * * *